United States Patent
Matsutani (10) Patent No.: US 11,572,464 B2
(45) Date of Patent: Feb. 7, 2023

(54) MEDICAL RUBBER COMPOSITION, MEDICAL RUBBER COMPONENT, AND PREFILLED SYRINGE

(71) Applicant: Sumitomo Rubber Industries, Ltd., Kobe (JP)

(72) Inventor: Yuichiro Matsutani, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 164 days.

(21) Appl. No.: 17/217,459

(22) Filed: Mar. 30, 2021

(65) Prior Publication Data
US 2021/0301116 A1    Sep. 30, 2021

(30) Foreign Application Priority Data
Mar. 31, 2020  (JP) .............................. JP2020-063679

(51) Int. Cl.
| | | |
|---|---|---|
| C08L 23/22 | (2006.01) | |
| A61M 5/31 | (2006.01) | |
| C08K 5/11 | (2006.01) | |
| C08K 5/14 | (2006.01) | |
| C08L 15/02 | (2006.01) | |
| C08L 9/00 | (2006.01) | |

(52) U.S. Cl.
CPC .............. *C08L 23/22* (2013.01); *A61M 5/31* (2013.01); *C08K 5/11* (2013.01); *C08K 5/14* (2013.01); *C08L 15/02* (2013.01); *A61M 2005/3104* (2013.01); *C08L 9/00* (2013.01); *C08L 2312/00* (2013.01)

(58) Field of Classification Search
CPC .... C08L 23/22; C08L 9/00; A61M 2005/3104
See application file for complete search history.

(56) References Cited

U.S. PATENT DOCUMENTS

| | | | |
|---|---|---|---|
| 2003/0100696 A1* | 5/2003 | Muraki | ................... A61L 2/081 526/348.7 |
| 2013/0137825 A1 | 5/2013 | Hochi et al. | |
| 2015/0086802 A1 | 3/2015 | Maeda et al. | |
| 2017/0296757 A1* | 10/2017 | Maeda | ..................... C08L 9/06 |

FOREIGN PATENT DOCUMENTS

| | | |
|---|---|---|
| JP | 3193895 B2 | 7/2001 |
| JP | 2001-340425 A | 12/2001 |
| JP | 2013-112703 A | 6/2013 |
| JP | 2015-62564 A | 4/2015 |
| WO | WO 2016/052037 A1 | 4/2016 |

\* cited by examiner

*Primary Examiner* — Mark S Kaucher
(74) *Attorney, Agent, or Firm* — Birch, Stewart, Kolasch & Birch, LLP (57) ABSTRACT

An object of the present invention is to provide a medical rubber composition having excellent non-elution characteristic and gas permeability. The present invention provides a medical rubber composition containing: (a) a butyl rubber, (b) a diene-based rubber containing polybutadiene, (c) a peroxide-based crosslinking agent, and (d) a co-crosslinking agent, wherein an amount of (b) the diene-based rubber in 100 parts by mass of the rubber component composed of (a) the butyl rubber and (b) the diene-based rubber is 15 parts by mass or more and 90 parts by mass or less, and a mass ratio ((d)/(c)) of (d) the co-crosslinking agent to (c) the peroxide-based crosslinking agent is 1.2 or more and 25 or less.

17 Claims, 2 Drawing Sheets

MEDICAL RUBBER COMPOSITION, MEDICAL RUBBER COMPONENT, AND PREFILLED SYRINGE

FIELD OF THE INVENTION

The present invention relates to a medical rubber composition, a medical rubber component using the same, and a prefilled syringe, more specifically relates to a technology for improving gas permeation of a medical rubber component.

DESCRIPTION OF THE RELATED ART

In recent years, from the viewpoint of prevention of medical malpractice, ease of handling during use and improved hygiene, application of a prefilled syringe having a pharmaceutical liquid prefilled in a sterilized syringe barrel tends to be expanded. For securing liquid-seal, air-seal, sterility and the like, a nozzle cap is attached to the tip on the nozzle side of the syringe barrel of the prefilled syringe.

Examples of the prefilled syringe include a syringe with a needle where a needle is buried into the nozzle of the syringe barrel in advance; and a syringe without a needle where the nozzle cap thereof is removed and an injection needle is attached. Examples of the nozzle cap include a needle-shielding type having a needle penetration portion for the syringe with a needle and covering the nozzle in a state that the needle is stuck into the needle penetration portion by several millimeters; and a type of covering the nozzle of the syringe without a needle (refer to JP 2013-112703 A, JP 2001-340425 A, JP 2015-62564 A, etc.).

The prefilled syringe is sterilized by ethylene oxide gas (EOG), steam, or gamma ray radiation in a state that the nozzle cap is attached to the nozzle of the syringe barrel before filling a pharmaceutical liquid. Then, the syringe barrel is filled with a pharmaceutical liquid in a sterile condition, and plugged with a sterilized gasket. After that, the prefilled syringe is packaged and shipped as a product.

In the gas sterilization using EOG or steam, the gas such as EOG and steam is required to permeate through the rubber forming the nozzle cap, for example, in a case of the syringe with a needle, to sterilize the whole needle including the tip stuck into the needle penetration portion, the nozzle, or the like.

After the EOG sterilization, it is required that the residue such as ethylene oxide used in the sterilization and ethylene glycol, ethylene chlorohydrin and the like which are secondary products of ethylene oxide, can be quickly removed by deaeration and/or aeration. In addition, it is required that after the steam sterilization the adsorbed moisture can be quickly removed by drying.

JP 3193895 B discloses a rubber stopper fora pharmaceutical container, obtained by vulcanizing a halogenated butyl rubber blended with a super high molecular weight polyethylene fine powder in an amount of from 5 to 25 parts by weight relative to 100 parts by weight of the halogenated butyl rubber, without the presence of a zinc compound and using at least one kind of 2-substitute-4,6-dithiol-s-triazine derivatives or an organic peroxide.

WO 2016/052037 discloses a nozzle cap for a prefilled syringe, wherein the nozzle cap is formed from a rubber composition containing a rubber component, the rubber component includes a diene-based rubber and a non-diene-based rubber, and a proportion of the diene-based rubber in 100 parts by mass of a total of the two rubbers is 20 parts by mass or more and 70 parts by mass or less.

In addition, several items such as non-elution, high cleanability, chemical resistance, needle penetration resistance, self-sealability and high slidability are required for a medical rubber stopper sealing an opening of a syringe. Qualities and properties required for a medical rubber stopper should comply with the infusion rubber stopper test of Japanese Pharmacopoeia, 17th Edition.

SUMMARY OF THE INVENTION

The present invention has been made in view of the above problems. An object of the present invention is to provide a medical rubber composition having gas permeability suitable for gas sterilization while maintaining non-elution.

The present invention provides a medical rubber composition containing (a) a butyl rubber, (b) a diene-based rubber containing polybutadiene, (c) a peroxide-based crosslinking agent, and (d) a co-crosslinking agent, wherein an amount of (b) the diene-based rubber is 15 parts by mass or more and 90 parts by mass or less in 100 parts by mass of the rubber component composed of (a) the butyl rubber and (b) the diene-based rubber, and a mass ratio ((d)/(c)) of (d) the co-crosslinking agent to (c) the peroxide-based crosslinking agent is 1.2 or more and 25 or less.

If the medical rubber composition according to the present invention is used, the medical rubber composition having excellent gas permeability for gas sterilization while maintaining non-elution characteristic, and the medical rubber component using the medical rubber composition are obtained. If the medical rubber composition according to the present invention is used, the nozzle cap having excellent gas permeability for gas sterilization while maintaining non-elution characteristic, and the prefilled syringe using the nozzle cap are obtained.

DESCRIPTION OF THE PREFERRED EMBODIMENT

The medical rubber composition according to the present invention contains (a) a butyl rubber, (b) a diene-based rubber containing polybutadiene, (c) a peroxide-based crosslinking agent, and (d) a co-crosslinking agent, wherein an amount of (b) the diene-based rubber is 15 parts by mass or more and 90 parts by mass or less in 100 parts by mass of the rubber component composed of (a) the butyl rubber and (b) the diene-based rubber, and a mass ratio ((d)/(c)) of (d) the co-crosslinking agent to (c) the peroxide-based crosslinking agent is 1.2 or more and 25 or less.

The medical rubber composition according to the present invention contains, (a) the butyl rubber and (b) the diene-based rubber containing polybutadiene, as the rubber component.

First, (a) the butyl rubber will be explained. As the butyl rubber, for example, a copolymer obtained by polymerizing isobutylene and a small amount of isoprene is preferable.

The butyl rubber preferably includes a halogenated butyl rubber. Examples of the halogenated butyl rubber include a chlorinated butyl rubber, a brominated butyl rubber, and a bromide of a copolymer of isobutylene and p-methylstyrene. As the halogenated butyl rubber, the chlorinated butyl rubber or the brominated butyl rubber is preferable. The chlorinated butyl rubber or brominated butyl rubber is, for example, obtained by an addition reaction or substitution reaction between chlorine or bromine and an isoprene moiety in a butyl rubber, specifically a double bond and/or a carbon atom adjacent to a double bond of the isoprene moiety.

The amount of halogen in the halogenated butyl rubber is preferably 0.5 mass % or more, more preferably 1 mass % or more, and even more preferably 1.5 mass % or more, and is preferably 5 mass % or less, more preferably 4 mass % or less, and even more preferably 3 mass % or less.

Specific examples of the chlorinated butyl rubber include at least one member selected from CHLOROBUTYL 1066 (stabilizer: NS, halogen content: 1.26%, Mooney viscosity: 38 $ML_{1+8}$ (125° C.), specific gravity: 0.92) available from Japan Butyl Co. Ltd. and LANXESS X_BUTYL CB1240 available from LANXESS Co. Ltd.

Specific examples of the brominated butyl rubber include at least one member selected from BROMOBUTYL 2255 (stabilizer: NS, halogen content: 2.0%, Mooney viscosity: 46 $ML_{1+8}$ (125° C.), specific gravity: 0.93) available from Japan Butyl Co. Ltd. and LANXESS X_BUTYL BBX2 available from LANXESS Co. Ltd.

The medical rubber composition according to the present invention contains (b) the diene-based rubber containing polybutadiene, as the rubber component. The diene-based rubber is obtained by polymerizing a diene monomer and is a rubber having a double bond in the main chain thereof. It is noted that in the present invention, (a) the butyl rubber that is the copolymer obtained by polymerizing isobutylene and a small amount of isoprene is not treated as a diene-based rubber, although a small amount of isoprene is copolymerized.

Examples of the diene-based rubber include a natural rubber (NR), an isoprene rubber (IR), a polybutadiene (BR), a styrene-butadiene rubber (SBR), a chloroprene rubber (CR), and an acrylonitrile-butadiene rubber (NBR). These rubbers may be used solely, two or more of these rubbers may be used in combination.

In the present invention, as the diene-based rubber, (b) the diene-based rubber containing polybutadiene is preferably used. The amount of the polybutadiene in the diene-based rubber is preferably 50 mass % or more, more preferably 70 mass % or more, and even more preferably 90 mass % or more. In addition, it is also preferable that the diene-based rubber consists of the polybutadiene.

In the medical rubber composition according to the present invention, the amount of (b) the diene-based rubber is 15 parts by mass or more, preferably 20 parts by mass or more, more preferably 40 parts by mass or more, and even more preferably 60 parts by mass or more, and is preferably 90 parts by mass or less, more preferably 85 parts by mass or less, even more preferably 80 parts by mass or less, and most preferably 75 parts by mass or less in 100 parts by mass of the rubber component composed of (a) the butyl rubber and (b) the diene-based rubber. If the amount of (b) the diene-based rubber falls within the above range, the gas permeability increases while maintaining the excellent non-elution characteristic. As a result, for example, it is possible to shorten the time of the gas sterilization process for the prefilled syringe before filling a pharmaceutical liquid.

The medical rubber composition according to the present invention contains (c) the peroxide-based crosslinking agent. (c) The peroxide-based crosslinking agent is blended mainly for crosslinking (b) the diene-based rubber.

(c) The peroxide-based crosslinking agent used in the present invention is an organic peroxide. The organic peroxide decomposes by heat or light to produce radicals. The radical generated from the organic peroxide abstracts a hydrogen atom from (b) the diene-based rubber to generate a radical in (b) the diene-based rubber. The radical of (b) the diene-based rubber is considered to become a starting point of crosslinking. In other words, (c) the peroxide-based crosslinking agent has an action of improving the crosslinking efficiency of (b) the diene-based rubber.

On the other hand, (c) the peroxide-based crosslinking agent has an action of softening (a) the butyl rubber during kneading. In other words, the rubber molecule of the butyl rubber is cut by the mechanical shearing during the kneading. In the present invention, (d) the co-crosslinking agent which will be described later is considered to have an action of bonding to the cut butyl rubber molecule and crosslinking the cut rubber molecules. As a result, degradation of the butyl rubber molecule is suppressed and the non-elution can be maintained.

Specific examples of (c) the peroxide-based crosslinking agent include a dialkyl peroxide, a peroxy ester, a peroxy ketal, and a hydroperoxide. Examples of the dialkyl peroxide include di(2-t-butylperoxyisopropyl) benzene, dicumyl peroxide, 2,5-dimethyl-2,5-di(t-butylperoxy) hexane, t-butylcumyl peroxy, di-t-hexylperoxy, di-t-butylperoxy, and 2,5-dimethyl-2,5-di(t-butylperoxy) hexyne-3. Examples of the peroxy ester include t-butylperoxy maleate, t-butylperoxy-3,3,5-trimethyl cyclohexanoate, t-butylperoxy laurate, t-butylperoxyisopropyl monocarbonate, t-hexylperoxy benzoate, 2,5-dimethyl-2,5-di(benzoylperoxy) hexane, t-butylperoxy acetate, and t-butylperoxy benzoate. Examples of the peroxy ketal include 1,1-di(t-hexylperoxy)-3,3,5-trimethyl-cyclohexane, 1,1-di(t-hexylperoxy) cyclohexane, 1,1-di(t-butylperoxy)-2-methylcyclohexane, 1,1-di(t-butylperoxy) cyclohexane, 2,2-di(t-butylperoxy) butane, n-butyl-4,4-di(t-butylperoxy) valerate, and 2,2-di(4,4-di(t-butylperoxy) cyclohexyl) propane. Examples of the hydroperoxide include p-menthane hydroperoxide, and diisopropylbenzene hydroperoxide. These organic peroxides may be used solely, or two or more of them may be used in combination.

The amount of (c) the peroxide-based crosslinking agent in the medical rubber composition according to the present invention is preferably 0.05 part by mass or more, more preferably 0.1 part by mass or more, and even more preferably 0.15 part by mass or more, and is preferably 7 parts by mass or less, more preferably 5 parts by mass or less, and even more preferably 2 parts by mass or less, with respect to 100 parts by mass of the rubber component composed of (a) the butyl rubber and (b) the diene-based rubber. If the amount of (c) the peroxide-based crosslinking agent falls within the above range, softening of the butyl rubber component is suppressed, and non-elution is maintained.

The medical rubber composition according to the present invention may contain a crosslinking agent other than (c) the peroxide-based crosslinking agent, as long as the crosslinking agent does not impair the inventive effect. Examples of the crosslinking agent other than (c) the peroxide-based crosslinking agent include sulfur, a metal oxide, a resin crosslinking agent, an organic peroxide, and a triazine derivative. They may be used solely, or two or more of them may be used in combination.

Examples of the sulfur used as the crosslinking agent include powder sulfur, fine powder sulfur, precipitated sulfur, colloidal sulfur, and chlorinated sulfur.

Examples of the metal oxide used as the crosslinking agent include magnesium oxide, calcium oxide, zinc oxide, and copper oxide.

Examples of the resin crosslinking agent include alkylphenol formaldehyde resins such as an alkylphenol formaldehyde resin, a thermo-reactive phenol resin, a phenol dialcohol-based resin, a bisphenol resin, and a thermo-reactive bromomethylalkylated phenol resin.

The medical rubber composition according to the present invention contains (d) the co-crosslinking agent. The co-crosslinking agent is considered to act on the radical of (b) the diene-based rubber formed by the peroxide-based crosslinking agent to form a crosslink. Further, the co-crosslinking agent suppresses cleavage of (a) the butyl rubber caused by (c) the peroxide-based crosslinking agent, to form a crosslink.

(d) The co-crosslinking agent preferably includes a polyfunctional (meth)acrylate compound. The polyfunctional (meth)acrylate compound more preferably includes a difunctional or higher functional (meth)acrylate-based compound, and even more preferably includes a trifunctional or higher functional (meth)acrylate-based compound, and preferably includes an octafunctional or lower functional (meth)acrylate-based compound, more preferably includes a hexafunctional or lower functional (meth)acrylate-based compound. Examples of the difunctional or higher functional (meth)acrylate compound include a compound having at least two acryloyl groups and/or methacryloyl groups. It is noted that "(meth)acrylate" means "acrylate" and/or "methacrylate".

Examples of the difunctional or higher functional (meth)acrylate-based compound include polyethylene glycol di(meth)acrylate, 1,4-butanediol di(meth)acrylate, 1,6-hexanediol di(meth)acrylate, 1,9-nonanediol di(meth)acrylate, trimethylolpropane tri(meth)acrylate, trimethylolethane tri(meth)acrylate, pentaerythritol tri(meth)acrylate, pentaerythritol tetra(meth)acrylate, glycerin tri(meth)acrylate, dipentaerythritol tri(meth)acrylate, dipentaerythritol tetra(meth)acrylate, dipentaerythritol penta(meth)acrylate, dipentaerythritol hexa(meth)acrylate, tripentaerythritol tetra(meth)acrylate, tripentaerythritol penta(meth)acrylate, tripentaerythritol hexa(meth)acrylate, and tripentaerythritol hepta(meth)acrylate. (d) The co-crosslinking agent may be used solely, or two or more of them may be used in combination.

In the present invention, as (d) the co-crosslinking agent, trimethylolpropane triacrylate and/or trimethylolpropane trimethacrylate is preferably used.

The amount of (d) the co-crosslinking agent in the medical rubber composition according to the present invention is preferably 0.1 part by mass or more, more preferably 0.4 part by mass or more, and even more preferably 0.6 part by mass or more, and is preferably 10 parts by mass or less, more preferably 5 parts by mass or less, and even more preferably 3 parts by mass or less, with respect to 100 parts by mass of the rubber component composed of (a) the butyl rubber and (b) the diene-based rubber. If the amount of (d) the co-crosslinking agent falls within the above range, softening of the butyl rubber component is suppressed, and non-elution is maintained.

In the medical rubber composition according to the present invention, a mass ratio ((d)/(c)) of (d) the co-crosslinking agent to (c) the peroxide-based crosslinking agent is preferably 1.2 or more, more preferably 1.5 or more, and even more preferably 2 or more, and is preferably 25 or less, more preferably 20 or less, and even more preferably 10 or less. If the mass ratio ((d)/(c)) of (d) the co-crosslinking agent to (c) the peroxide-based crosslinking agent falls within the above range, softening of the butyl rubber component is suppressed, and non-elution is maintained.

The medical rubber composition according to the present invention may contain a triazine derivative. It is considered that the triazine derivative actions as a crosslinking agent on (a) the butyl rubber and actions as a crosslinking retarder on the crosslinking system using (c) the peroxide-based crosslinking agent/(d) the co-crosslinking agent. Examples of the triazine derivative include a compound represented by the general formula (1).

(1)

[In the formula, R is —SH, —OR$^1$, —SR$^2$, —NHR$^3$ or —NR$^4$R$^5$ (R$^1$, R$^2$, R$^3$, R$^4$ and R$^5$ represent an alkyl group, an alkenyl group, an aryl group, an aralkyl group, an alkylaryl group or a cycloalkyl group, and R$^4$ and R$^5$ may be identical to or different from each other); M$^1$ and M$^2$ are H, Na, Li, K, ½Mg, ½Ba, ½Ca, an aliphatic primary amine, secondary amine or tertiary amine, a quaternary ammonium salt or a phosphonium salt; and M$^1$ and M$^2$ may be identical to or different from each other.]

In the general formula (1), examples of the alkyl group include an alkyl group having 1 to 12 carbon atoms such as methyl group, ethyl group, n-propyl group, isopropyl group, n-butyl group, isobutyl group, tert-butyl group, n-pentyl group, isopentyl group, tert-pentyl group, n-hexyl group, 1,1-dimethylpropyl group, octyl group, isooctyl group, 2-ethylhexyl group, decyl group, and dodecyl group. Examples of the alkenyl group include an alkenyl group having 1 to 12 carbon atoms such as vinyl group, allyl group, 1-propenyl group, isopropenyl group, 2-butenyl group, 1,3-butadienyl group, and 2-pentenyl group. Examples of the aryl group include a monocyclic or condensed polycyclic aromatic hydrocarbon group, and specific examples thereof include an aryl group having 6 to 14 carbon atoms such as phenyl group, naphthyl group, anthryl group, phenanthryl group, and acenaphthylenyl group. Examples of the aralkyl group include an aralkyl group having 7 to 19 carbon atoms such as benzyl group, phenethyl group, diphenylmethyl group, 1-naphthylmethyl group, 2-naphthylmethyl group, 2,2-diphenylethyl group, 3-phenylpropyl group, 4-phenylbutyl group, 5-phenylpentyl group, 2-biphenylylmethyl group, 3-biphenylylmethyl group, and 4-biphenylylmethyl group. Examples of the alkylaryl group include an alkylaryl group having 7 to 19 carbon atoms such as tolyl group, xylyl group, and octylphenyl group. Examples of the cycloalkyl group include a cycloalkyl group having 3 to 9 carbon atoms such as cyclopropyl group, cyclobutyl group, cyclopentyl group, cyclohexyl group, cycloheptyl group, cyclooctyl group and cyclononyl group.

Specific examples of the triazine derivative represented by the general formula (1) include 2,4,6-trimercapto-s-triazine, 2-methylamino-4,6-dimercapto-s-triazine, 2-(n-butylamino)-4,6-dimercapto-s-triazine, 2-octylamino-4,6-dimercapto-s-triazine, 2-propylamino-4,6-dimercapto-s- triazine, 2-diallylamino-4,6-dimercapto-s-triazine, 2-dimethylamino-4,6-dimercapto-s-triazine, 2-dibutylamino-4,6-dimercapto-s-triazine, 2-di(iso-butylamino)-4,6-dimercapto-s-triazine, 2-dipropylamino-4,6-dimercapto-s-triazine, 2-di(2-ethylhexyl) amino-4,6-dimercapto-s-triazine, 2-dioleylamino-4,6-dimercapto-s-triazine, 2-laurylamino-4,6-dimercapto-s-triazine, 2-anilino-4,6-dimercapto-s-triazine, and sodium salt or disodium salt thereof.

Among them, 2,4,6-trimercapto-s-triazine, 2-dialkylamino-4,6-dimercapto-s-triazine, and 2-anilino-4,6-dimercapto-s-triazine are preferable, and 2-dibutylamino-4,6-dimercapto-s-triazine is most preferable in view of easy availability.

In the present invention, the triazine derivative may be used solely, or two or more of the triazine derivatives may be used in combination.

The medical rubber composition according to the present invention preferably does not contain a vulcanization accelerator. This is because the vulcanization accelerator may remain in the final rubber product, and dissolve into the pharmaceutical liquid in a syringe or vial. Examples of the vulcanization accelerator include a guanidine accelerator (e.g. diphenylguanidine), a thiuram accelerator (e.g. tetramethylthiuram disulfide, tetramethylthiuram monosulfide), a dithiocarbamate accelerator (e.g. zinc dimethyldithiocarbamate), a thiazole accelerator (e.g. 2-mercaptobenzothiazole, dibenzothiazyl disulfide), and a sulfenamide accelerator (e.g. N-cyclohexyl-2-benzothiazole sulfenamide, N-t-butyl-2-benzothiazole sulfenamide).

The medical rubber composition according to the present invention may contain a hydrotalcite. The hydrotalcite functions as an anti-scorching agent when crosslinking the halogenated butyl rubber, and also functions as an agent to prevent increase in compression permanent strain of the medical rubber member. Further, the hydrotalcite also functions as an acid acceptor to absorb chlorine-based gas or bromine-based gas happening when crosslinking the halogenated butyl rubber and prevent occurrence of crosslinking inhibition caused by these gases. It is noted that the above-mentioned magnesium oxide is also capable of functioning as an acid acceptor.

Examples of the hydrotalcite include one or at least two members selected from a Mg—Al hydrotalcite such as $Mg_{4.5}Al_2(OH)_{13}CO_3.3.5H_2O$, $Mg_{4.5}Al_2(OH)_{13}CO_3$, $Mg_4Al_2(OH)_{12}CO_3.3.5H_2O$, $Mg_6Al_2(OH)_{16}CO_3.4H_2O$, $Mg_5Al_2(OH)_{14}CO_3.4H_2O$ and $Mg_3Al_2(OH)_{10}CO_3.1.7H_2O$.

Specific examples of the hydrotalcite include DHT-4A (registered trademark)-2 available from Kyowa Chemical Industry Co. Ltd.

In the medical rubber composition, when the hydrotalcite is used as the acid acceptor, the hydrotalcite is preferably used together with MgO. In this case, the amount of the hydrotalcite is preferably considered as the total amount of the acid acceptor (hydrotalcite and MgO). The total amount of the acid acceptor (hydrotalcite and MgO) is preferably 0.5 part by mass or more, more preferably 1 part by mass or more, and is preferably 15 parts by mass or less, more preferably 10 parts by mass or less, with respect to 100 parts by mass of the rubber component composed of (a) the butyl rubber and (b) the diene-based rubber. If the total amount of the acid acceptor (hydrotalcite and MgO) falls within the above range, rusting of a mold or the like is suppressed, and defects that the materials themselves become white spot of foreign material are reduced.

The medical rubber composition according to the present invention may further contain (e) a filler. Examples of (e) the filler include an inorganic filler such as clay and talc, and a resin powder of an olefin resin, styrene elastomer or ultra-high molecular weight polyethylene (UHMWPE). Among them, as the filler, the inorganic filler is preferable, and clay or talc is more preferable. The filler functions as adjusting the rubber hardness of the medical rubber component, and also functions as a weight increasing material to reduce the production cost of the medical rubber component.

Examples of the clay include calcined clay and kaolin clay. Specific examples of the clay include SILLITIN (registered trademark) Z available from Hoffmann Mineral Corporation, SATINTONE (registered trademark) W available from Engelhard Corporation, NN Kaolin Clay available from Tsuchiya Kaolin Industry Co. Ltd., and PoleStar 200R available from IMERYS Specialities Japan K.K.

Specific examples of the talc include Hytron A available from Takehara Kagaku Kogyo Co., Ltd., MICRO ACE (registered trademark) K-1 available from Nippon Talc Co. Ltd., and Mistron (registered trademark) Vapor available from IMERYS Specialities Japan K.K.

The amount of (e) the filler in the medical rubber composition according to the present invention is preferably appropriately set according to the desired rubber hardness or the like of the medical rubber component. The amount of (e) the filler in the medical rubber composition according to the present invention is, for example, preferably 5 parts by mass or more, more preferably 10 parts by mass or more, and even more preferably 20 parts by mass or more, and is preferably 200 parts by mass or less, more preferably 150 parts by mass or less, and even more preferably 100 parts by mass or less, with respect to 100 parts by mass of the rubber component composed of (a) the butyl rubber and (b) the diene-based rubber.

The medical rubber composition according to the present invention may further contain a coloring agent such as titanium oxide and carbon black, a lubricant such as stearic acid and low density polyethylene (LDPE), a processing aid, polyethylene glycol acting as a crosslinking activator, or the like, in an appropriate proportion.

The present invention includes a medical rubber component formed from the medical rubber composition according to the present invention. Examples of the medical rubber component according to the present invention include a rubber stopper or sealing component of a container for various medical preparations such as a liquid preparation, a powder preparation and a freeze-dried preparation; and a sliding or sealing component such as a rubber stopper for a vacuum blood collecting tube, and a plunger stopper or nozzle cap for a prefilled syringe.

The medical rubber composition according to the present invention is obtained by kneading (a) the butyl rubber, (b) the diene-based rubber containing polybutadiene, (c) the peroxide-based crosslinking agent, (d) the co-crosslinking agent, and other optional materials added where necessary. The kneading can be performed, for example, with an open roll, a closed kneader, or the like. The kneaded mixture is preferably molded into a ribbon shape, a sheet shape, a pellet shape, or the like, and is more preferably molded into the sheet shape.

The kneaded mixture in the ribbon shape, sheet shape or pellet shape is press-molded to form a medical rubber component having a desired shape. The crosslinking reaction of the medical rubber composition proceeds during the pressing. The molding temperature is, for example, preferably 130° C. or more, more preferably 140° C. or more, and is preferably 200° C. or less, more preferably 190° C. or less. The molding time is preferably 2 minutes or more, more preferably 3 minutes or more, and is preferably 60 minutes or less, more preferably 30 minutes or less. The molding pressure is preferably 0.1 MPa or more, more preferably 0.2 MPa or more, and is preferably 10 MPa or less, more preferably 8 MPa or less.

The extra part of the molded product obtained by the press molding is cut off and removed to form a predetermined shape. The obtained molded product is washed, sterilized, dried and packed to produce the medical rubber component.

In addition, as usual, a resin film may be laminated on and integrated with the medical rubber component. Examples of the resin film include a film of an inactive resin such as polytetrafluoroethylene (PTFE), tetrafluoroethylene-ethylene copolymer (ETFE), their modified products, and ultra-high density polyethylene (UHMWPE).

The resin film may be integrated with the medical rubber component formed by press molding, for example, by press molding the resin film in a state of being laminated on the sheet-shaped rubber composition.

The rubber hardness of the medical rubber component according to the present invention is preferably 35 or more and is preferably 70 or less in Durometer type A hardness (Shore A hardness) measured in accordance with the measuring method described in "Durometer hardness, Part III, Measuring method of hardness, Vulcanized rubber and thermoplastic rubber" of Japan Industry Specification JIS K 6253-3: 2012.

The Shore A hardness of a sliding or sealing component such as a plunger stopper or a nozzle cap for a prefilled syringe is preferably 40 or more and is preferably 70 or less. It is noted that a needle-shielding type nozzle cap for a syringe with a needle most preferably has a Durometer type A hardness of 55 or less, for more easily sticking the needle into the needle penetration portion and further surely preventing bending of the needle.

On the other hand, a nozzle cap for a syringe without a needle most preferably has a Durometer type A hardness of 40 or more, for further enhancing the sealability of the nozzle cap covering the nozzle during storage of the nozzle cap, or further surely preventing loosening of the nozzle cap and falling of the nozzle cap from the nozzle.

The rubber hardness of the medical rubber component is adjusted, for example, by varying the mixing ratio of the raw materials.

The gas permeability (cc·cm/cm$^2$·sec·cmHg) of the medical rubber component formed from the medical rubber composition according to the present invention, per a thickness of 1 mm of the sample, measured by Method B (isopiestic method) prescribed in "Gas permeability test method for plastic films and sheets" of Japan Industry Specification JIS K7126-1987, is preferably $1.5 \times 10^{-10}$ or more, more preferably $3.0 \times 10^{-10}$ or more, and even more preferably $5.0 \times 10^{-10}$ or more, and is preferably $100 \times 10^{-10}$ or less, more preferably $50 \times 10^{-10}$ or less, and even more preferably $30 \times 10^{-10}$ or less. The gas permeability is adjusted to the above range by varying the proportions of various materials. The gas permeability is preferably measured by using, for example, $N_2$.

If the gas permeability falls within the above range, good gas permeability is ensured. During the EOG sterilization, EOG can quickly permeate through the nozzle cap to sterilize the nozzle or needle in a short time. In addition, during the deaeration and/or aeration, the residue such as ethylene oxide, ethylene glycol and ethylene chlorohydrin can be quickly decreased, and the sterilization time is shortened, which improve the productivity of the prefilled syringe. In addition, if the gas permeability is excessively great, a general gas permeates so much during normal storage excluding the sterilization that the sealing property deteriorates.

Further, the internal pressure generated inside the nozzle cap during the deaeration and/or aeration can be quickly released to prevent the nozzle cap from loosening and falling from the nozzle.

The rubber component formed from the medical rubber composition according to the present invention is suitably used as a nozzle cap for a prefilled syringe. In addition, the present invention includes the prefilled syringe comprising the nozzle cap according to the present invention. The prefilled syringe according to the present invention is preferably sterilized by gas in a state that the nozzle cap is attached to the syringe.

It is noted that the nozzle cap is sometimes called by a name of, for example, needle cap, needle shield, rubber cap, tip cap, plunger tip or syringe sealing stopper, depending on the attached form.

Examples of the gas sterilization include steam sterilization, and ethylene oxide gas (EOG) sterilization treatment.

The EOG sterilization treatment is a method of sterilizing a device at an atmosphere of ethylene oxide gas. The concentration of the ethylene oxide gas preferably ranges from 400 mg/l to 1100 mg/l, more preferably ranges from 450 mg/l to 900 mg/l, and even more preferably ranges from 500 mg/l to 700 mg/l. If the concentration of the ethylene oxide gas is excessively high, the residual concentration of the EOG gas tends to be high after the sterilization. In addition, the EOG sterilization temperature preferably ranges from 35° C. to 70° C., and the sterilization humidity (relative humidity) is preferably 40% RH or more.

Figure 1:
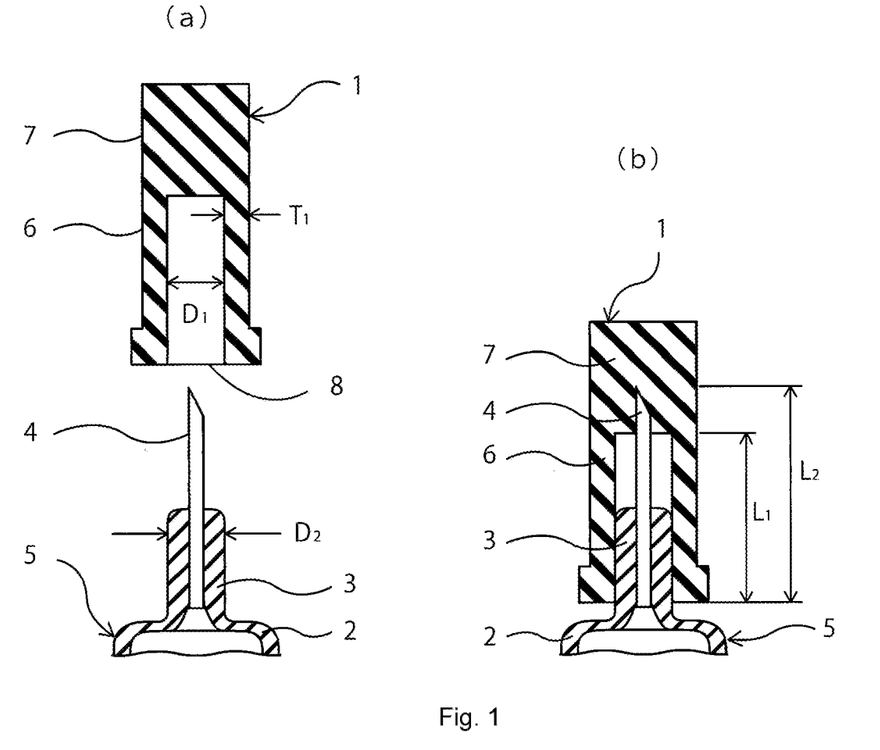
FIG. 1 is a figure illustrating one embodiment (nozzle cap) of the medical rubber component according to the present invention.

FIG. 1(a) is a cross-sectional view showing one example of an embodiment of the nozzle cap according to the present invention and a nozzle of a syringe barrel, wherein the nozzle is covered with the nozzle cap. FIG. 1(b) is a cross-sectional view showing a state of covering the nozzle with the nozzle cap of FIG. 1(a).

The nozzle cap 1 is used for a syringe 5 with a needle in which a needle 4 is buried into the nozzle 3 of a syringe barrel 2 in advance. The nozzle cap 1 as a whole is integrally formed from the medical rubber composition. The nozzle cap 1 comprises a cylindrical portion 6 having an inner diameter D1 slightly less than an outer diameter D2 of the nozzle 3, and a needle penetration portion 7 connecting to one end side (upper end side in the figure) of the cylindrical portion 6.

The needle penetration portion 7 is formed into a columnar shape having an outer surface continuous to the cylindrical portion 6. An opening 8 for inserting the nozzle 3 in the cylindrical portion 6 and covering the nozzle 3 with the nozzle cap 1, is formed on another end side (lower end side in the figure) of the cylindrical portion 6.

A size L1 from the closed end coupled to the needle penetration portion 7 to another end on the side of the opening 8, in the axis direction of the cylindrical portion 6, and a size L2 from the another end on the side of the opening 8 to the tip of the needle 4, of the cylindrical portion 6 in a state of the nozzle cap 1 covering the nozzle 3, are set to L1<L2, by which the tip of the needle 4 sticks in the needle penetration portion 7 by about 5 mm to secure liquid-seal, air-seal, sterility, or the like.

Figure 2:
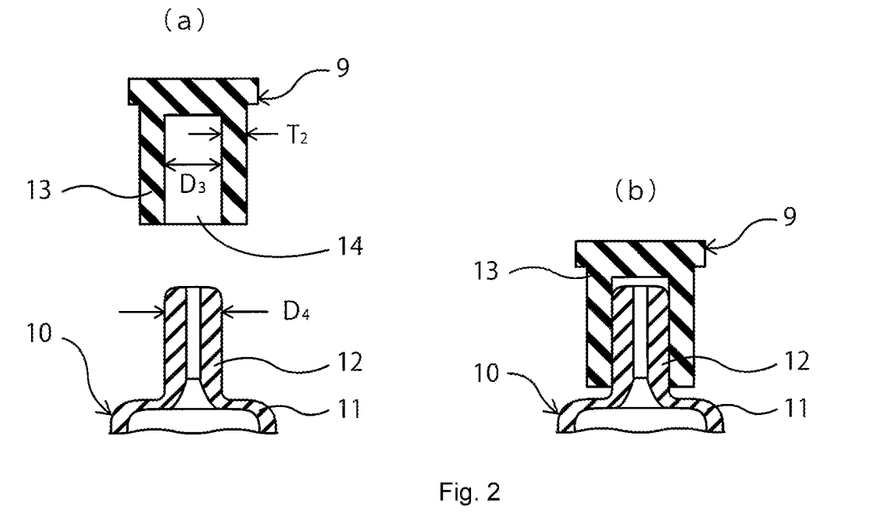
FIG. 2 is a figure illustrating one embodiment (nozzle cap) of the medical rubber component according to the present invention.

FIG. 2(a) is a cross-sectional view showing another example of an embodiment of the nozzle cap according to the present invention and a nozzle of a syringe barrel, wherein the nozzle is covered with the nozzle cap. FIG. 2(b)

is a cross-sectional view showing a state of covering the nozzle with the nozzle cap of FIG. 2(a).

The nozzle cap 9 is used to cover the nozzle 12 of a syringe barrel 11 of a syringe 10 without a needle. The nozzle cap 9 is integrally formed from the above medical rubber composition. The nozzle cap 9 comprises a cylindrical portion 13 having an inner diameter D3 slightly less than an outer diameter D4 of the nozzle 12.

An end side (upper end side in the figure) of the cylindrical portion 13 is closed, and an opening 14 for inserting the nozzle 12 in the cylindrical portion 13 and covering the nozzle 12 with the nozzle cap 9, is formed on another end side (lower end side in the figure) of the cylindrical portion 13.

The thinnest regions of the nozzle caps 1, 9, i.e. the thickness T1 of the cylindrical portion 6 in the example of FIG. 1(a), (b) and the thickness T2 of the cylindrical portion 13 in the example of FIG. 2(a)(b), are preferably set to 1.0±0.5 mm, respectively.

If the thicknesses T1, T2 are higher than the above range, permeation of gas or steam is suppressed, thus the EOG sterilization, the deaeration and/or aeration, the steam sterilization, or the drying process after the steam sterilization needs longer time, which may lower the productivity of the prefilled syringe.

Further, the internal pressure generated inside the nozzle caps 1, 9 during the deaeration and/or aeration or during the steam sterilization or the drying process thereof fails to be quickly released, thus the nozzle caps 1, 9 may become loose and easily fall from the nozzles 3, 12 by the elevated internal pressure. On the other hand, if the thicknesses T1, T2 are lower than the above range, rigidity is insufficient, and poor closing may occur when covering the nozzle 3, 12 with the nozzle caps 1, 9, which may lower the productivity of the prefilled syringe.

Compared to these, if the thicknesses T1, T2 fall within the above range, the nozzle caps 1, 9 are provided with good gas permeability, and in particular, EOG can quickly permeate through the nozzle caps 1, 9 to sterilize the nozzles 3, 12 or the needle 4 in a short time during the EOG sterilization, and the residue such as ethylene oxide, ethylene glycol and ethylene chlorohydrin can be quickly removed during the deaeration and/or aeration, which improve the productivity of the prefilled syringe.

Further, the internal pressure generated inside the nozzle caps 1, 9 during the deaeration and aeration can be quickly released to prevent the nozzle caps 1, 9 from loosening and falling from the nozzles 3, 12.

Furthermore, the nozzle caps 1, 9 are provided with appropriate rigidity, and poor closing hardly occurs when covering the nozzle 3, 12 with the nozzle caps 1, 9, which improve the productivity of the prefilled syringe.

Examples

Next, the present invention will be described in detail by way of examples. However, the present invention is not limited to the examples described below. Various changes and modifications without departing from the spirit of the present invention are included in the scope of the present invention.

[Preparation of Medical Rubber Composition]

Materials shown in Table 1 were kneaded to prepare medical rubber compositions. The kneading was performed at 20° C. for about 10 minutes using an open roll.

TABLE 1-1

| | Medical rubber composition No. | 1 | 2 | 3 | 4 | 5 | 6 | 7 |
|---|---|---|---|---|---|---|---|---|
| (a) | Butyl rubber | 100 | 90 | 0 | 30 | 30 | 30 | 30 |
| (b) | Polybutadiene rubber | 0 | 10 | 100 | 70 | 70 | — | 70 |
| (b) | Isoprene rubber | — | — | — | — | — | 70 | — |
| Filler | MIPELON | 5 | 5 | 5 | 5 | 5 | 5 | 5 |
| | Hydrotalcite | 1 | 1 | 1 | 1 | 1 | 1 | 1 |
| | Magnesium oxide | 2 | 2 | 2 | 2 | 2 | 2 | 2 |
| | Titanium oxide | 1 | 1 | 1 | 1 | 1 | 1 | 1 |
| | Silica | 10 | 10 | 10 | 10 | 10 | 10 | 10 |
| | Talc | 10 | 10 | 10 | 10 | 10 | 10 | 10 |
| | Stearic acid | 0.3 | 0.3 | 0.3 | 0.3 | 0.3 | 0.3 | 0.3 |
| | PEG 400 | 0.5 | 0.5 | 0.5 | 0.5 | 0.5 | 0.5 | 0.5 |
| | Carbon black | 0.15 | 0.15 | 0.15 | 0.15 | 0.15 | 0.15 | 0.15 |
| (c) | Peroxide-based crosslinking agent | 0.2 | 0.2 | 0.2 | 0.2 | 0.2 | 0.2 | 0.2 |
| (d) | Co-crosslinking agent | 1 | 1 | 1 | 0.14 | 7.5 | 1 | 0.2 |
| | (d)/(c) | 5 | 5 | 5 | 0.7 | 37.5 | 5 | 1 |
| | Triazine derivative | 1 | 1 | 1 | 1 | 1 | 1 | 1 |
| $N_2$ gas permeability | | | | | | | | |
| | cc · cm/cm$^2$ · sec · cmHg | 6.39E−11 | 1.21E−10 | 3.10E−09 | Not conducted | 1.35E−09 | 1.30E−09 | 1.39E−09 |
| | Index evaluation | 1 | 1.9 | 48.5 | — | 21.1 | 20.3 | 21.8 |
| | Relative evaluation | P | P | G | — | G | G | G |
| Eluting material performance | | | | | | | | |
| | Potassium permanganate reducing substance (mL/100 mL) | 0.1 | 0.2 | 1.5 | Not conducted | 0.7 | 1.5 | 1.6 |
| | Relative evaluation | G | G | P | — | G | P | P |
| | EOG sterilization test (hour) | >10 | >10 | 3 | Not conducted | Not conducted | 3 | 3 |
| | Relative evaluation | | | | — | — | | |

Formulation: parts by mass

TABLE 1-2

| Medical rubber composition No. | | 8 | 9 | 10 | 11 | 12 | 13 | 14 |
|---|---|---|---|---|---|---|---|---|
| (a) | Butyl rubber | 80 | 70 | 30 | 20 | 10 | 30 | 30 |
| (b) | Polybutadiene rubber | 20 | 30 | 70 | 80 | 90 | 70 | 70 |
| (b) | Isoprene rubber | — | — | — | — | — | — | — |
| Filler | MIPELON | 5 | 5 | 5 | 5 | 5 | 5 | 5 |
| | Hydrotalcite | 1 | 1 | 1 | 1 | 1 | 1 | 1 |
| | Magnesium oxide | 2 | 2 | 2 | 2 | 2 | 2 | 2 |
| | Titanium oxide | 1 | 1 | 1 | 1 | 1 | 1 | 1 |
| | Silica | 10 | 10 | 10 | 10 | 10 | 10 | 10 |
| | Talc | 10 | 10 | 10 | 10 | 10 | 10 | 10 |
| | Stearic acid | 0.3 | 0.3 | 0.3 | 0.3 | 0.3 | 0.3 | 0.3 |
| | PEG 4000 | 0.5 | 0.5 | 0.5 | 0.5 | 0.5 | 0.5 | 0.5 |
| | Carbon black | 0.15 | 0.15 | 0.15 | 0.15 | 0.15 | 0.15 | 0.15 |
| (c) | Peroxide-based crosslinking agent | 0.2 | 0.2 | 0.2 | 0.2 | 0.2 | 0.2 | 0.2 |
| (d) | Co-crosslinking agent | 1 | 1 | 1 | 1 | 1 | 5 | 0.24 |
| | (d)/(c) | 5 | 5 | 5 | 5 | 5 | 25 | 1.2 |
| | Triazine derivative | 1 | 1 | 1 | 1 | 1 | 1 | 1 |
| $N_2$ gas permeability | | | | | | | | |
| | cc·cm/cm$^2$·sec·cmHg | 1.80E-10 | 2.90E-10 | 1.50E-09 | 2.10E-09 | 2.72E-09 | 1.28E-09 | 1.38E-09 |
| | Index evaluation | 2.8 | 4.5 | 23.5 | 32.9 | 42.6 | 20 | 21.6 |
| | Relative evaluation | F | F | G | G | G | G | G |
| Eluting material performance | | | | | | | | |
| | Potassium permanganate reducing substance (mL/100 mL) | 0.3 | 0.6 | 0.7 | 1.1 | 1.4 | 0.6 | 1.4 |
| | Relative evaluation | G | G | G | F | F | G | F |
| | EOG sterilization test (hour) | 10 | 6 | 3 | 3 | 3 | 3 | 3 |
| | Relative evaluation | F | G | G | G | G | G | G |

Formulation: parts by mass

Details of the materials used above are as follows.

Butyl rubber: HT-1066 (chlorinated butyl rubber) available from Exxon Mobil Corporation Polybutadiene rubber: BR-1220 available from Zeon Corporation Isoprene rubber: IR-2200 available from Zeon Corporation MIPELON: ultra-high molecular weight polyethylene powder XM-220 available from Mitsui Chemicals, Inc.

Hydrotalcite: ALCAMIZER 1 available from Kyowa Chemical Industry Co., Ltd.

Magnesium oxide: KYOWAMAG available from Kyowa Chemical Industry Co., Ltd.

Titanium oxide: TIPAQUE A100 available from Ishihara Sangyo Kaisha, Ltd.

Silica: Nipsil LP available from Tosoh Silica Corporation

Talc: Mistron Vapor available from IMERYS Specialities K.K

Stearic acid: NNA-180 available from NOF Corporation

PEG 4000: polyoxyethylene glycol (average molecular weight: 3100, freezing point: 55° C.) available from NOF Corporation Carbon black: Thermal MT available from Cancarb Limited Peroxide-based crosslinking agent: Perhexa 25B-40 available from NOF Corporation Co-crosslinking agent: trimethylol propane triacrylate (TMPT) available from Shin-nakamura Chemical Co., Ltd.

Triazine derivative: Disnet DB available from Sankyo Kasei Sangyo Co., Ltd.

[Evaluation Method]

(1) Gas Permeation Coefficient (cc·cm/cm$^2$·sec·cmHg)

A testing piece for measuring gas permeation coefficient was prepared from the obtained medical rubber composition, and the gas permeation coefficient was measured. The measurement was performed according to JIS-K 6275-1 by a differential pressure method, using GTR-30XASR available from GTR Corporation.

Testing gas: $N_2$

Testing sample: A slab with a thickness of from 0.5 mm to 1.0 mm was prepared by press molding the rubber composition at the temperature of 180° C. for 6 minutes.

<Relative Evaluation>

The rubber composition No. 1 was adopted as a standard formulation and the $N_2$ permeation coefficient thereof was defined as 1, and the $N_2$ permeation coefficient of each rubber composition was represented by converting the $N_2$ permeation coefficient of each rubber composition into this index.

G (Good): 5 or more

F (Fair): 2 or more and less than 5

P (Poor): less than 2

(2) Eluting Material Test

Testing sample: A slab with a thickness of 2 mm was prepared by press molding the above-blended rubber composition at a temperature of 180° C. for 6 minutes. The slab was punched with a punch having φ17 mm to obtain a testing sample.

Regarding the produced sample, "Eluting Material Test" described in "7.03 Test method for an infusion rubber stopper" of Japanese Pharmacopoeia, 17$^{th}$ Edition, was performed. The optimized conditions were as follows.

State of testing liquid: colorless and transparent

UV transmittance: transmittances in a layer length of 10 mm at a wave length of 430 nm and a wave length of 650 nm were not lower than 99.0%.

Ultraviolet absorption spectrum: absorption at a wave length of 220 nm to 350 nm was not higher than 0.20.

pH: difference between the testing liquid and a blank testing liquid was not higher than 1.0.

Zinc: absorbance of the testing liquid was not higher than that of the standard liquid.

Potassium permanganate reducing substance: not higher than 2.0 mL/100 mL (Specification of Japanese Pharmacopoeia)

Evaporation residue: not higher than 2.0 mg

<Relative Evaluation>

In the Table, it is described as "G (Good)" when the concentration of potassium permanganate reducing substance was less than 1.0 mL/100 mL, it is described as "F (Fair)" when the concentration of potassium permanganate reducing substance was 1.0 mL/100 mL or more and 1.4 mL/100 mL or less, and it is described as "P (Poor)" when the concentration of potassium permanganate reducing substance was more than 1.4 mL/100 mL.

(3) Ethylene Oxide Gas (EOG) Sterilization Test

Figure 3:
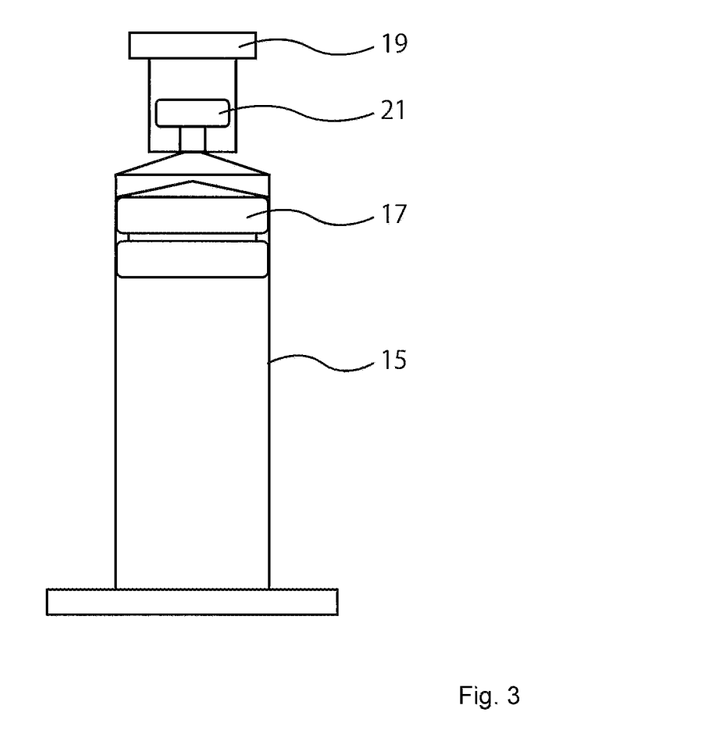
FIG. 3 is a figure illustrating a sample for EOG sterilization test.

A testing syringe of FIG. 3 was produced. As the material of the syringe body (barrel) 15, a cycloolefin polymer (COP) resin available from Daisei Chemical Industry Co. Ltd. was used, and the syringe stopper 17 was formed from a general medical rubber composition using a butyl rubber. The nozzle cap 19 was formed from the medical rubber composition in Table 1. BI (*Bacillus atrophaeus* ATCC cell 9372) 21 was used as the bacterium and set as shown in FIG. 3, and the nozzle cap 19 was attached, to produce the syringe sample for the EOG sterilization test. As the measuring apparatus, STN-062 available from CROSSTEX Corporation was used, the testing syringe sample was sterilized for a predetermined time at 50° C. under an EOG atmosphere, and the number of BI bacteria was measured.

<Relative Evaluation>

Ten specimens were used for each of the medical rubber compositions, and the sterilization test was conducted for the specimens. The ten specimens were evaluated by the time required by the sterilization treatment to kill the bacterium. In the table, it is shown as "G (Good)" when the sterilization time is 6 hours or less, it is shown as "F (Fair)" when the sterilization time is more than 6 hours and 10 hours or less, and it is shown as "P (Poor)" when the sterilization time is more than 10 hours.

Results of the gas permeability, eluting material test and EOG sterilization test are shown in Table 1.

It can be seen from Table 1 that the medical rubber component formed from the medical rubber composition according to the present invention has excellent non-elution and gas permeability. The medical rubber composition No. 1 failed to be sterilized in 24 hours. The medical rubber composition No. 2 failed to be sterilized in 10 hours. The medical rubber composition No. 4 had a small mass ratio ((d)/(c)) of (d) the co-crosslinking agent to (c) the peroxide-based crosslinking agent, and the rubber composition failed to be crosslinked. The medical rubber composition No. 5 had a great mass ratio ((d)/(c)) of (d) the co-crosslinking agent to (c) the peroxide-based crosslinking agent, and thus the sample for the EOG sterilization test failed to be formed.

This application is based on Japanese Patent application No. 2020-063679 filed on Mar. 31, 2020, the contents of which are hereby incorporated by reference.

The invention claimed is:

1. A medical rubber composition containing:
    (a) a butyl rubber,
    (b) a diene-based rubber containing polybutadiene,
    (c) a peroxide-based crosslinking agent, and
    (d) a co-crosslinking agent,
    wherein an amount of (b) the diene-based rubber is 15 parts by mass or more and 90 parts by mass or less in 100 parts by mass of a rubber component composed of (a) the butyl rubber and (b) the diene-based rubber, and
    a mass ratio ((d)/(c)) of (d) the co-crosslinking agent to (c) the peroxide-based crosslinking agent is 1.2 or more and 25 or less.

2. The medical rubber composition according to claim 1, wherein (a) the butyl rubber includes a halogenated butyl rubber.

3. The medical rubber composition according to claim 2, wherein the halogenated butyl rubber includes a chlorinated butyl rubber.

4. The medical rubber composition according to claim 1, wherein the amount of (b) the diene-based rubber is 20 parts by mass or more and 90 parts by mass or less in 100 parts by mass of the rubber component composed of (a) the butyl rubber and (b) the diene-based rubber.

5. The medical rubber composition according to claim 1, wherein an amount of (c) the peroxide-based crosslinking agent is 0.05 part by mass or more and 7 parts by mass or less with respect to 100 parts by mass of the rubber component composed of (a) the butyl rubber and (b) the diene-based rubber.

6. The medical rubber composition according to claim 1, wherein an amount of (d) the co-crosslinking agent is 0.1 part by mass or more and 10 parts by mass or less with respect to 100 parts by mass of the rubber component composed of (a) the butyl rubber and (b) the diene-based rubber.

7. The medical rubber composition according to claim 1, wherein (d) the co-crosslinking agent includes a polyfunctional (meth)acrylate compound.

8. A medical rubber component formed from a medical rubber composition containing:
    (a) a butyl rubber,
    (b) a diene-based rubber containing polybutadiene,
    (c) a peroxide-based crosslinking agent, and
    (d) a co-crosslinking agent,
    wherein an amount of (b) the diene-based rubber is 15 parts by mass or more and 90 parts by mass or less in 100 parts by mass of a rubber component composed of (a) the butyl rubber and (b) the diene-based rubber, and
    a mass ratio ((d)/(c)) of (d) the co-crosslinking agent to (c) the peroxide-based crosslinking agent is 1.2 or more and 25 or less.

9. The medical rubber component according to claim 8, wherein (a) the butyl rubber includes a halogenated butyl rubber.

10. The medical rubber component according to claim 9, wherein the halogenated butyl rubber includes a chlorinated butyl rubber.

11. The medical rubber component according to claim 8, wherein the amount of (b) the diene-based rubber is 20 parts by mass or more and 90 parts by mass or less in 100 parts by mass of the rubber component composed of (a) the butyl rubber and (b) the diene-based rubber.

12. The medical rubber component according to claim 8, wherein an amount of (c) the peroxide-based crosslinking agent is 0.05 part by mass or more and 7 parts by mass or less with respect to 100 parts by mass of the rubber component composed of (a) the butyl rubber and (b) the diene-based rubber.

13. The medical rubber component according to claim 8, wherein an amount of (d) the co-crosslinking agent is 0.1 part by mass or more and 10 parts by mass or less with respect to 100 parts by mass of the rubber component composed of (a) the butyl rubber and (b) the diene-based rubber.

14. The medical rubber component according to claim 8, wherein (d) the co-crosslinking agent includes a polyfunctional (meth)acrylate compound.

15. A nozzle cap for a prefilled syringe, formed from a medical rubber composition containing:
   (a) a butyl rubber,
   (b) a diene-based rubber containing polybutadiene,
   (c) a peroxide-based crosslinking agent, and
   (d) a co-crosslinking agent,
   wherein an amount of (b) the diene-based rubber is 15 parts by mass or more and 90 parts by mass or less in 100 parts by mass of a rubber component composed of (a) the butyl rubber and (b) the diene-based rubber, and
   a mass ratio ((d)/(c)) of (d) the co-crosslinking agent to (c) the peroxide-based crosslinking agent is 1.2 or more and 25 or less.

16. A prefilled syringe comprising a nozzle cap, wherein the nozzle cap is formed from a medical rubber composition containing:
   (a) a butyl rubber,
   (b) a diene-based rubber containing polybutadiene,
   (c) a peroxide-based crosslinking agent, and
   (d) a co-crosslinking agent,
   an amount of (b) the diene-based rubber is 15 parts by mass or more and 90 parts by mass or less in 100 parts by mass of the rubber component composed of (a) the butyl rubber and (b) the diene-based rubber, and
   a mass ratio ((d)/(c)) of (d) the co-crosslinking agent to (c) the peroxide-based crosslinking agent is 1.2 or more and 25 or less.

17. The prefilled syringe according to claim 16, wherein the prefilled syringe is sterilized by gas in a state that the nozzle cap is attached to the syringe.

* * * * *